United States Patent [19]

Chuman et al.

[11] Patent Number: 4,871,537

[45] Date of Patent: Oct. 3, 1989

[54] 6,12-DIMETHYLPENTADECAN-2-ONE AND ITS USE IN MONITORING AND CONTROLLING THE BANDED CUCUMBER BEETLE

[75] Inventors: Tatsuji Chuman, Tokyo, Japan; Paul L. Guss, deceased, late of Brookings, S. Dak., by Patricia Guss, executrix; Robert E. Doolittle, Gainesville, Fla.; John R. McLaughlin, Gainesville, Fla.; James H. Tumlinson, III, Gainesville, Fla.

[73] Assignee: The United States of America as represented by the Secretary of Agriculture, Washington, D.C.

[21] Appl. No.: 207,591

[22] Filed: Jun. 16, 1988

[51] Int. Cl.$^4$ ............................................. A01N 35/02
[52] U.S. Cl. ..................................... 424/84; 568/382; 514/675
[58] Field of Search .......................... 568/382; 424/84; 514/675

[56] References Cited

U.S. PATENT DOCUMENTS 4,474,991 10/1984 Guss et al. ........................... 568/382
4,734,524 3/1988 Guss et al. ........................... 560/265

OTHER PUBLICATIONS

F. P. Cuthbert, Jr., and W. J. Reid, Jr., "Studies of Sex Attractant of Banded Cucumber Beetle," *Journal of Economic Entomology* 57: 247-250 (1964).

M. Schwarz, M. Jacobson, and F. P. Cuthbert, Jr., "Chemical Studies of the Sex Attractant of the Banded Cucumber Beetle," *Journal of Economic Entomology* 64: 769-770 (1971).

P. L. Guss, J. H. Tumlinson, P. E. Sonnet, and A. T. Proveaux, "Identification of a Female-Produced Sex Pheromone of the Western Corn Rootworm," *Journal of Chemical Ecology* 8: 545-556 (1982).

P. L. Guss, J. H. Tumlinson, P. E. Sonnet, and J. R. McLaughlin, "Identification of a Female-Produced Sex Pheromone From the Southern Corn Rootworm, *Diabrotica undecimpunctata howardi* Barker," *Journal of Chemical Ecology* 9: 1363-1375 (1983).

*Primary Examiner*—James H. Reamer
*Attorney, Agent, or Firm*—M. Howard Silverstein; John D. Fado; Margaret A. Connor

[57] ABSTRACT

A pheromonal compound produced by the banded cucumber beetle has been identified as 6,12-dimethylpentadecan-2-one. Both the synthetically prepared racemic compound and the purified natural pheromone elicited responses by banded cucumber males in field tests. By attracting adult beetles to field traps, this compound is a useful tool for the monitoring and controlling of this major agricultural pest.

10 Claims, No Drawings

6,12-DIMETHYLPENTADECAN-2-ONE AND ITS USE IN MONITORING AND CONTROLLING THE BANDED CUCUMBER BEETLE

BACKGROUND OF THE INVENTION

1. Field of the Invention

This invention relates to a novel compound and use thereof for insect control, and more particularly to the novel pheromone compound 6,12-dimethylpentadecan-2-one and its use as an attractant, disruptant, and monitoring agent for the banded cucumber beetle.

2. Description of the Art.

Diabrotica is a large New World genus of *galerucine chrysomelids* that includes several pests. The catalog of Wilcox (*Coleopterorum Catalogus Supplementa.* (Ed. 2) *Galerucinae luperini:* Pars 78, *Fisc.* 2: 296–431 (1972)) lists 338 species in three groups; the *virgifera* and *fucata* groups includes pests. The banded cucumber beetle (BCB), *Diabrotica balteata* LeConte (Coleoptera: Chrysomelidae), is an economically important pest of vegetable and field crops, particularly sweet potato and seedling vine crops such as squash, melon, and cucumber (cucurbits). It occurs from the southern United States to Colombia, Venezuela, and Cuba. The adults feed on foliage and pollen while the larvae, which are the most damaging stage, feed on plant roots or tubers. They seriously threaten potato and sweet potato production in tropical and subtropical climates by scarring the tubers or edible roots which lowers market value or by subjecting the tubers/roots to infection by rot organisms. Larval feeding on curcurbits, corn, tomato, a wide range of peas and beans and many other vegetable hosts can reduce the vigor of the plant and thus reduce yield. Control of this pest involves the use of broad spectrum pesticides that often cause outbreaks of secondary pests or present risks of ground water contamination. Therefore, it is highly desirable to control BCB populations by other means.

The continued search for alternatives to the widespread applications of insecticides has led to the investigation of sex attractants as potential agents for use in integrated pest management. programs. A number of economically important insects are currently monitored, partially controlled, or completely controlled by use of their own specific pheromone. The use of pheromones has also been reported for locating, surveying, or monitoring pest populations at levels not otherwise detectable. In the case of the BCB, the lack of identification and availability of the BCB pheromone has precluded application of this technology to the treatment of this pest.

Cuthbert and Reid (*Journal of Economic Entomology* 57: 247–250 (1964)) reported that a natural sex attractant was produced by BCB females and that field traps baited with either adult virgin females or with their abdominal extracts attracted BCB males from distances as far as 49 feet. Schwarz et al. (*Journal of Economic Entomology* 64: 769–770 (1971)) carried out chemical studies on the active fraction of an extract of BCB adult virgin females. From their studies, they concluded that the BCB sex attractant included n-dodecenyl, ethylene epoxy, and methyl ketone moieties. They were unable to complete the structure elucidation.

Sex pheromones for some species of Diabrotica have been reported. Guss et al. (*Journal of Chemical Ecology* 9: 1363–1375 (1983) and U.S. Pat. No. 4,474,991) identified the R-enantiomer of 10-methyl-2-tridecanone as the sex pheromone of the southern corn rootworm (SCR), *D. undecimpunctata howardi* Barber. Guss et al. (*Journal of Chemical Ecology* 8: 545–556 (1982) and U.S. Pat. No. 4,734,5214) identified 8-methyl-2-decanol propanoate as the sex pheromone for the western corn rootworm (WCR), *D. virgifera virgifera* LeConte. The compound has been shown to be an effective attractant for adult males of the WCR; the northern corn rootworm, *D. longicornis barberi* Smith and Lawrence; and the Mexican corn rootworm, *D. virgifera zea* Krysan and Smith.

SUMMARY OF THE INVENTION

We have now for the first time obtained in pure or substantially pure form the major female-produced sex pheromone of the BCB. This new compound, identified as 6,12-dimethylpentadecan-2-one, has been isolated from virgin females of the BCB and has also been successfully synthesized. Traps baited with the natural and synthesized pheromone caught BCB males indicating that the compound is a sex pheromone of the BCB.

The novel compound provides a sensitive tool for detection of the BCB and provides a means for population control and population density estimation of this pest. Its usefulness in eliciting a behavioral response when applied to a locus of BCB males suggests the following economic applications: (1) the detection of infestation outbreaks; (2) the monitoring of existing adult populations in order to predict infestation levels the following year for scheduling of treatment with larval insecticides; and (3) the control of reproduction in adult populations either by direct disruption of mating through confusing or inhibitory properties, or by attracting a demographically significant portion of the male population for subsequent destruction or sterilization.

In accordance with this discovery it is an object of the invention to identify a unique sex pheromone from a representative of the family Chrysomelidae, and more particularly from the genus Diabrotica and the species *balteata*.

It is also an object of the invention to produce racemic 6,12-dimethylpentadecan-2-one as the synthetic sex pheromone of the BCB and to provide a synthesis procedure to prepare the racemic compound.

A further object of the invention is to utilize 6,12-dimethylpentadecan-2=one as a detection, monitoring, or control agent for this major agricultural pest.

Another object of the invention is to provide a BCB sex pheromone for use with insecticides, biological control agents and the like to attract and combat the pest.

Other objects and advantages of this invention will become readily apparent from the ensuing description.

BRIEF DESCRIPTION OF THE DRAWINGS

FIG. 1 (A) shows the chemical ionization ($CH_4$) and (B) electron impact mass spectra of BCB pheromone.

FIG. 2 shows the 300-mHZ proton magnetic resonance spectrum of approximately 3 $\mu$g of the purified natural BCB pheromone.

FIG. 3 shows the electron impact mass spectrum of the hydrogenolysis product of BCB pheromone.

FIG. 4 shows the synthesis of racemic 6,12-dimethylpentadecan-2-one. (i) $C_3H_7MgBr$; (ii) HBr; (III) $H_2/PtO_2/CH_3COOH$; (iv) Li; (v) CuI; (vi) methylvinylketone/(n-Bu)$_3$P; (vii) n-BuLi; (viii) $H_2$/Pd-C/ETOH; (ix) $H_2SO_4$.

DETAILED DESCRIPTION OF THE INVENTION

The novel compound of the invention, 6,12-dimethylpentadecan-2-one, is characterized by the following structural formula:

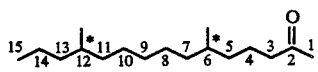

The novel compound was isolated from volatiles of BCB virgin females. The structure was elucidated by spectroscopic analyses and confirmed by synthesis. The biological and chemical data show that 6,12-dimethylpentadecan-2-one is the major component of the female-produced sex pheromone of the BCB. The material functions as a sex pheromone in that it is produced by one sex, and elicits an overt series of behaviors (activation, orientation, etc.) only by the opposite sex.

The structure is highly specific. The synthetic pheromones of the BCB and SCR were tested in the same area at the same time where good populations of both species existed; the BCB pheromone caught only BCB males and the SCR pheromone caught only SCR males, indicating the high specificity of each pheromone.

It is apparent from the structure that the compound may exist as any of four stereochemical configurations by virtue of chiral carbons 6 and 12. The racemic mixture containing the four stereoisomers of the compound can be prepared synthetically as described in detail below in Example 2. The scarcity of the natural isolate coupled with the inherent difficulty and economic disincentive of producing single enantiomers by directed stereochemical synthesis tends to favor the synthetic racemic 6,12-dimethylpentadecan-2-one for commercial utilization. The racemic compound is active in the same dose range as the purified natural pheromone in eliciting responses by BCB males to field traps. Thus, the racemic compound provides an economical source of the pheromone for commercial use.

As used in the specification and the claims, the phrase "pure or substantially pure" means with regards to the synthetic material that the novel compound is substantially free of compounds other than the stereoisomers of 6,12-dimethylpentadecan-2-one, and in cases where the compound has been obtained from BCB volatiles purity is equal or greater than that obtained in accordance with the isolation procedure outlined in Example 1.

ISOLATION OF THE NATURAL PHEROMONE

The novel compound was isolated from the volatiles of BCB virgin females as described in detail below in Example 1. Briefly, the insect volatiles were obtained by drawing air over BCB females and collecting the volatiles on an adsorbent. The hexane-ether extracts of the adsorbent from the collection chamber elicited behaviors from BCB males in the laboratory bioassy that indicated the presence of the female sex pheromone.

IDENTIFICATION OF THE NATURAL PHEROMONE

The identification of the novel compound of the invention is described in detail in Example 1, below. Identification of the novel compound presented problems of unusual difficulty. Identification of the novel compound was particularly difficult in part because no precedent for this structure existed. Prior to the invention, this compound was not known. Thus, its spectra were not available for computer spectral matching. Further, as discussed in detail below, the structure could not be predicted from known sex pheromones or attractants for the family Diabrotica. In addition to lack of precedent of structure assignment, another difficulty in the identification of the compound was that only limited amounts, about 10 $\mu$g, of the isolated compound were available, thus limiting investigations to use of gas chromatography/mass spectrometry (GC/MS) and nuclear magnetic resonance (NMR) spectroscopy which employed microanalytical techniques. Final elucidation of the compound required reduction of the pheromonal compound to its carbon skeleton by hydrogenolysis and use of deductive reasoning to select a candidate compound for testing.

As stated above, the structure of the BCB sex pheromone could not be predicted from known pheromones for other species of Diabrotica. The closest known Diabrotica pheromone is that identified for the SCR, namely 10-methyl-2-tridecanone (Guss et al., 1983, supra). Although both the pheromone for the BCB and the SCR have a ketone functional group on the second carbon of the chain and a methyl branch on the fourth carbon from the other end of the hydrocarbon chain, the BCB pheromone has two more carbons in the chain than the SCR pheromone, and furthermore it contains an additional methyl branch. Both chemical ionization (CI) and electron impact (EI) mass spectra together with high resolution proton nuclear magnetic resonance (PMR) were required to establish these facts. However, the task remained to establish the location of the second methyl branch. There was absolutely no precedent to suggest where it might be located, and the spectral data were insufficient to establish its location also. Thus, even after the gross structure was determined by MS and NMR, the number of possible structures was enormous. Elucidation of the compound required the reduction of the pheromonal compound to its carbon skeleton by hydrogenolysis and to obtain a mass spectrum of the product to establish the location of the methyl branches. Even then two possibilities existed, and one was chosen as the most likely candidate by deductive reasoning. The structure was then confirmed by synthesizing the candidate compound and comparing its chromatographic and spectral properties and its biological activity with those of the natural product. Difficulty of identification of this compound is further illustrated by the fact that of the moieties suggested by Schwarz et al. supra as occurring in this compound, only the suggestion of a methyl ketone moiety was correct.

In the identification procedure, identification was guided by laboratory bioassay of the fractions. Bioassay of the fractions obtained by preparative gas-liquid chromatography (GLC) indicated that the pheromonal activity was confined to a single peak eluting at 11 minutes on "OV-101" column under the experimental conditions described in Example 1. Further micropreparative chromatography on a "Carbowax 20M" packed column yielded a compound with a purity of greater than 99.5% by analysis on "OV-101" and "Carbowax 20M" capillary columns. The retention indices (Kovats, *Adv. Chromatogr.* 1: 229–235 (1965)) of this compound, relative to paraffin hydrocarbons, on the "OV-101" and "Carbowax 20M" capillary GLC columns were 1787 and 2114, respectively.

The following structural information was elucidated from the spectral data. The methane CI mass spectrum (FIG. 1A) established that the molecular weight of the compound was 254 with diagnostic peaks at m/e 253 (M −1), 255 (M +1), 283 (M +29), and 295 (M +41). In the EI mass spectrum (FIG. 1B), the peak at m/e 254 (M+) confirmed the molecular weight.

The [$^1$H]NMR spectrum of the purified natural pheromone (FIG. 2) supported the above assignment. The signals at δ1.64 (CH$_3$CO—; 3H, s) and 1.92 (—COCH$_2$—; 2H, t) confirmed the presence of a 2-oxobutyl moiety in the pheromone molecule. Furthermore, when expanded, the group of peaks from δ 0.86 to 0.91 appeared to consist of three overlapping signals, δ 0.875 (3H, d, J =8.1 Hz), 0.895 (3H, d, J =8.1 Hz), and 0.905 (3H, t, J =6.2 Hz) which suggests the presence of two methyl branches and a terminal methyl in the molecule.

Hydrogenolysis of the pheromone in the GC injector leading to the mass spectrometer source and EI mass spectral analysis of the product yielded the spectrum shown in FIG. 3. The peak at 240 (M+) confirms the 17-carbon skeleton indicated by mass spectra of the parent compound. The peaks at m/e 70, 71, and 197 and at m/e 98, 99, and 169 are of greater intensity than would be expected in a normal hydrocarbon and represent preferred cleavage on either side of two methyl branches. These data support a structure with methyl branches on carbons 4 and 10 as indicated in FIG. 3. The only other possible structure, with methyl branches on carbons 4 and 6, was ruled to because of the relative intensities of the peaks at m/e 98 and 99. The greater intensity of the peak at 98 is consistent with cleavage of the bond between carbons 9 and 10 in 4,10-dimethylpentadecane, with the fragment ion containing only one methyl branch. Cleavage between carbons 6 and 7 of 4,6-dimethylpentadecane yielding a fragment ion containing two methyl branches would be expected to produce peaks at m/e 98 and 99, but the peak at 99 should be of greater intensity. Thus the structure of the hydrogenolysis product was established as 4,10-dimethylpentadecane. Since the EI mass and PMR spectra of the pheromone indicated that the carbons α and β to the carbonyl must be unsubstituted, the only possible structure is 6,12-dimethylpentadecan-2-one.

SYNTHESIS

The novel synthesis of racemic 6,12-dimethylpentadecan-2-one is shown in FIG. 4 and described in detail below in Example 2. Briefly, the synthesis of racemic 6,12-dimethylpentadecan-2-one was initiated by the reaction of methylcyclopropyl ketone with n-propylmagnesium bromide. The intermediate tertiary carbinol was isomerized to the homoallylic bromide (1) with hydrobromic acid. The allic bromide (1) was reduced to 1-bromo-4-methylheptane (2) by hydrogenation with PtO$_2$. The saturated bromide (2) was converted to the corresponding organocopper reagent which was reacted with methyl vinyl ketone in the presence of tri-n-butyl phosphine to produce 8-methylundecan-2-one (3). A Wittig reaction between the C-12 methylketone (3) and ethylene ketal pentan-2-one phosphonium salt (4), produced a mixture of the Z and E isomers of the ethylene ketal of 6,12-dimethyl-(5) (15% yield). The unsaturated ethylene ketals were hydrogenated and then subjected to acid hydrolysis to produce 6,12-dimethylpentadecan-2-one (7). The final product was purified by high-performance liquid chomatography (HPLC) and GLC.

The CI and EI mass spectra and the PMR spectrum of pure synthetic racemic 6,12-dimethylpentadecan-2-one were identical with those of the isolated natural pheromone. Additionally the synthetic and natural pheromones cochromatographed, producing only one peak, on each of the two capillary GLC columns.

USES OF THE COMPOUND

The pure of substantially pure pheromone may be used as a detecting agent, monitoring agent, or control agent for adult beetles. In practice, 6,12-dimethylpentadecan-2-one is used as a trap bait or is otherwise applied to a locus of the adults in an amount effective to induce the desired male response. In the case of an attractant response, for example, an effective amount is defined as that quantity of compound which provides a release rate of the compound that attracts beetle males to the location of a bait at a rate significantly higher than males are attracted to a nonbaited location. Factors such as population density, temperature, wind velocity, and release rate will influence the response of the beetles and thus the actual number of beetles trapped. Factors such as temperature, wind velocity, and type of pheromone disseminator will influence release rate. The amount of compound in a particular set of circumstances that will provide a release rate within an effective range can readily be determined by a dose response field test. As described below in Example 3 and shown in Table 3, we have found that in Florida, when using rubber septa, a release rate in the range of 23 to 476 ng/hour is effective.

In the case where the desired response is disruption of mating by confusing or inhibiting the beetle, an effective amount is defined as that quantity of compound which provides a release rate of the compound that permeates the atmosphere such that males are prevented from orienting to and inseminating the females, i.e., disruption of mating, at a rate significantly higher than disruption of mating of males at a nontreated location. As with the attractant response, factors such as population density, temperature, wind velocity, and release rate will influence the actual number of beetles disrupted. The exact dose to use in any particular set of circumstances can readily be determined by a dose response field test.

It is envisioned that 6,12-dimethylpentadecan-2-one would be useful in detecting, monitoring, or controlling BCB populations when used in conjunction with a trap or pheromone disseminator known in the art. Exemplary of such a trap is the stick trap. Illustrative of pheromone disseminators are rubber septa and capillaries. Typically, the compound is applied to the release substrate in solution in hexane or other suitable carrier or undiluted. Volatilization can be retarded by inclusion of a material that has a higher molecular weight than 6,12-dimethylpentadecan-2-one and that does not interfere with the activity of the pheromone. Slow release may also be effected by encapsulation or absorption into a porous substrate.

When used as a detection or monitoring agent, traps are baited with the novel compound of the invention and the catch tabulated to determine size and location of infestation. Economic use of appropriate pest management systems can then be determined.

Use of the pheromone as a control agent can be carried out in several ways. One method is to use the compound to attract the insects to suitable substrates and subsequently or simultaneously expose the beetles to insecticides which control the beetle. An effective amount of the insecticide is used, that is, an amount that is lethal for an exposed insect or at least sublethal but sufficient to incapacitate the insect in regard to mating activity. Exemplary of such an insecticide is carbaryl (1-naphthyl N-methylcarbamate) (sold under the tradename "Sevin" by Rhone-Poulenc Ag. Co. Inc., Research Triangle Park, NC). Insecticides can be used in traps baited with the pheromone. This eliminates the need to spread the insecticides unnecessarily. It is also envisioned that chemosterilants could be used in conjunction with the pheromone compound to attract and sterilize male beetles.

Another method to control beetles using the novel compound is to detect the location and boundaries of localized beetle infestations and employ in the area biological control agents such as parasites or predators of the BCB.

6,12-Dimethylpentadecan-2-one may also be used to control BCB by confusion of BCB males, thus preventing mating. For example, one technique is to permeate the atmosphere with sufficient compound to prevent males from orienting to and inseminating the females.

Another use of the compound is as a reference compound, particularly in the area of natural product chemistry. The availability of a synthetic standard would assist in the identification of pheromones from other species of other Diabrotica.

Other uses of the novel compound will be obvious to those in the art.

EXAMPLES

The following examples are intended only to further illustrate the invention and are not intended to limit the scope of the invention which is defined by the claims.

EXAMPLE 1

Isolation of Natural Pheromone

Insect Rearing and Handling. The insects were from a laboratory colony maintained at the Northern Grain Insects Laboratory, Brookings, SD., by the method of Jackson, in *Handbook of Insect Rearing*, Eds. Singh and Moore, Elsevier, Amsterdam, 1985, pp. 237–254. The colony was begun in Brookings, in August 1981, with eggs obtained from a laboratory colony at the U.S. Department of Agriculture, Agriculture Research Service, Vegetable Insects Research Laboratory, Charleston, SC. Virgin females were isolated from males within 24 hours of emergence and held in screened cages (30×30×30 cm) for three days before being placed in the pheromone collection chamber.

Collection of BCB Volatiles. The pheromone collection system and methods were the same as those used to collect volatiles from the SCR, Guss et al., 1973, supra. The collection was performed at 24° C. with a 12-hour photophase, and the pheromone was collected on "Porpak Q" (sold by Alltech Associates Inc., Deerfield, Ill.) (Byrne et al., *Journal of Chemical Ecology* 1: 1–7 (1975)).

Laboratory Bioassay. During the initial isolation stages, a laboratory bioassay similar to that described by Guss et al., 1982, supra, was employed. In this array, four or five virgin male beetles were placed in a Petri dish (150×15-mm) and allowed to acclimate for 15 minutes. A test extract or fraction in 1-5 μl of hexane was applied to a 5-mm$^2$ piece of filter paper, the solvent was evaporated for about 10 minutes, and then the paper was placed into the disk. Responses of beetles toward the treated paper, antennal waving, and copulatory behavior were considered evidence of the presence of the pheromone.

Pheromone Purification. Volatiles were extracted from "Porapak Q" filters with 50 ml of ether-hexane (60:40) by agitation for 24 hours. The extract was concentrated with a stream of N$_2$, and the concentrate was subjected to preparative GLC without further treatment.

Micropreparative GLC was performed with a Varian Model 1400 gas chromatograph equipped with a flame ionization detector. The pheromone was purified was two packed columns: 10% dimethyl silicone (sold under the tradename "OV-101" by Supelco. Bellefonte, Pa.) on 60-80 mesh diatomaceous earth (sold under the tradename "Chromosorb W:" by Supelco, Bellefonte, Pa.) (glass column 2 ×2 mm ID) and 7.5% polyglycol (sold under the tradename "Carbowax 20M" by Supelco, Bellefonte, Pa.) on 60–80 mesh "Chromosorb W" (glass column 2 m×2mm ID). The injection port and column temperatures were both 200° C. when operating the "OV-101" column and 180° C. when operating the "Carbowax 20M" column. Detector temperature was 250° C. The carrier gas (He) flow rate through each column was 20 ml/min.

The chromatograph was modified to accommodate a 90:10 effluent splitter and an external, dry ice-acetone-cooled fraction collector (Brownlee and Silverstein, *Analytical Chemistry* 40: 2077–2079 (1968)). Fractions were collected in 1.5-mm (ID)×305-mm glass capillary tubes and eluted with about 10 μl of hexane.

Pheromone Analysis and Identification. Natural pheromone was analyzed on 50-m×0.25-mm-ID fused silica capillary columns in a Hewlett-Packard model 5790 gas chromatograph equipped with a split-splitless injector system (30-second split delay) at a carrier gas (He) linear flow rate of 18 cm/sec. The "OV-101" column was operated at 60° C. for 1 minute after injection, temperature programmed at 30° C./min to 200° C., and then operated isothermally. The "Carbowax 20M" column was operated at 60° C. for 2 minutes after injection, programmed at 30° C./min to 210° C., and then operated isothermally.

Mass spectra were obtained with Nermag R10-10 mass spectrometer equipped with a chemical ionization/electron impact source and interfaced with a Varian Vista model 6000 gas chromatograph equipped with a split-splitless injection system. Samples were introduced into the mass spectrometer source through a 50-m×0.25-mm-ID fused silica "OV-101" column operated at 6020 C. for 2 minutes, then programmed at 3220 C./min to 230° C., and then operated isothermally. The linear flow velocity of the carrier gas (He) was 18 cm/sec. The spectrometer was interfaced with a Digital PDP 11/23 computer for collection and analysis of the data.

Hydrogenoloysis in the inlet of the GC interfaced to the mass spectrometer was performed by the method of Beroza and Sarmiento, *Analytical Chemistry* 35: 1353-1357 (1963) and *Analytical Chemistry* 36: 1744–1750 (1964). About 6 cm of a glass insert (1 mm ID) was filled with 1% neutral Pd catalyst on diatomaceous earth) (sold under the tradename "Gaschrom W" by Alltech Associates Inc., Deerfield, Ill.) and placed in the injection port ahead of the "OV-101" column. The catalyst was maintained at 285° C. for the hydrogenolysis, and H$_2$ was used as the carrier gas at a flow rate of 20 ml/min.

PMR analysis was performed with a Nicolet 300 MHz Fourier transform NMR spectrometer interfaced to a Nicolet model 1280 data system (16K data points, 10 μsex pulse). Samples purified by micropreparative GLC (about 3 μg total pheromone) were transferred from the glass capillary, using benzene-D6, into an NMR tube, the top of which was 5 mm (OD), with a 50×2-mm (OD) coaxial extension on the bottom ((Wilmad Glass Co., Buena, NJ., catalog No. 507 with WGS-5BL stem).

The CI and EI mass spectra are shown in FIGS. 1A and 1B, respectively. The NMR spectrum is shown in FIG. 2, and the EI mass spectrum of the hydrogenolysis product is shown in FIG. 3. As discussed above, the spectra support the identification of the pheromone as 6,12-dimethylpentadecan-2-one.

EXAMPLE 2

Synthesis of 6,12-Dimethylpentadecan-2-one

The synthesis of racemic 6,12-dimethylpentadecan-2-one is shown in FIG. 4 and described below.

1-Bromo-4-methyl-3-heptene (1). Methyl cyclopropyl ketone was allowed to react with n-propyl magnesium bromide. The intermediate tertiary carbinol was isomerized to the homoallylic bromide (1) with hydrobromic acid. It was prepared in 79% yield; b.p. 68–70° C. at 7 mm. The IR and NMR spectra of the compound were in complete agreement with its assigned structure.

1-Bromo-4-methylheptane (2). This was prepared from compound (1) in 70% yield by hydrogenation over platinum oxide in glacial acetic acid: b.p. 67°–70° C. at 8.5 mm; NMR (CDCl$_3$) 0.86 (t, CH$_3$CH$_2$), 0.87 (d, CH$_3$CH), 3.40 (m, 2H, CH$_2$CH$_2$Br)). The IR and NMR spectra of the compound were in complete agreement with the assigned structure and reported values.

8-Methyl-undecan-2-one (3). The lithium reagent was prepared from 9.66 g (0.05 M) of bromide (2), and 0.853 g (0.123 M) of lithium metal in 50 ml of dry ether at −15 to −20° C. and 100 μl of methyl iodide was used to start the reaction. This lithium reagent was converted into an organocopper reagent and reacted with freshly distilled methyl vinyl ketone in the presence of tri-n-butylphosphine by the method of Suzuki et al., *Tetrahedron Letters* 21: 1247–1250 (1980). Distillation afforded 80% yield of product; b.p. 58°–60° C. at 0.5 mm; CI-MS (CH$_4$) m/z, 185 (M +1); IR (CCl$_4$), 2960(s), 2940(s), 2880(s), 2860(s), 1723(s), 1468(m), 1380(m), 1358(m), 1160(m); NMR (CDCl$_3$), 0.84 (6H, m), 1.1–1.4 (11H, m), 1157 (2H, m), 2.12 (3H, s), 2.41 (2H, t).

4-Oxo-pentane Ethylene Ketal triphenylphosphonium Bromide (4). The phosphonium salt was prepared by an adaptation of the method of Sonnet et al., *Journal of Chemical Ecology* 13: 547–555 (1987) as follows: 5-chloro-2-pentanone ethylene ketal (Aldrich Chemical Company) (4.12 g, 25 mmol), sodium iodide (7.5 g, 50 mmol), triphenylphosphine (6.56 g, 25 mmol), and a trace of anhydrous K$_2$CO$_3$ were heated together under reflux in 50 ml of acetonitrile for 64 hours. After cooling to room temperature, the precipitated solid was removed by filtration and washed two times with small portions of acetonitrile. The solvent was removed from the filtrate by rotary evaporation, and the residual crude product was triturated several times with 1,2-dichloroethylene (DCE). The combined triturate was filtered and the filtrate concentrated. Anhydrous ether was added and the precipitated solid was collected by filtration and washed with a little anhydrous ether. The white solid was slurried in heptane and the solvent removed by rotary evaporation (to remove traces of DCE) producing a white solid in 60% yield: IR (CHCl$_3$), 2950(s), 1438(s), 1110(s), 1030(m), 690(m), 660(m), NMR (CDCl$_3$), 1.22 (3H, s), 1.58 (2H, bds), 1.75 (2H, m), 2.05 (2H, t), 3.9 (4H, s), 7.8 (15H, m).

6,12-Dimethyl-5-pentadecen-2-one Ethylene Ketal (5). A hexane solution of n-butylithium (19.0 ml, 0.038 M) was added dropwise at 0.C to a suspension of 20 g (0.038 M) ketal phosphonium bromide (4) in dry THF and stirred for 30 minutes. The reaction mixture as brought to room temperature, and 3.6 g (0.02 M) of 8-methylundecan-2-one (3) in ether was added dropwise and the mixture was stirred for 6 hours. The reaction mixture was poured into ice water, and the mixture was extracted with hexane. The hexane solution was washed with water and saturated NaCl and dried over Na$_2$SO$_4$. Distillation furnished 870 mg (15% yield) of 6,12-dimethyl-5-pentadecen-2-one ethylene ketal (5); b.p. 120°–130° C. at 0.7 mm Hg; CI-MS (CH$_4$) (m/z), 297 (M +1); IR(CCl$_4$), 2960(s), 2940(s), 2880(s), 1467(m), 1380(m), 1240(m), 1160(m), 1220(m), 1090(m), 1060(m), 950(m), 900(m); NMR (CDCl$_3$), 0.85 (6H, m), 1.1–1.7 (17H, m), 1.68 (3H, s), 2.05 (2H, m), 2.13 (3H, s),3.95 (4H, bds), 5.10 (1H, m).

6,12-Dimethylpentadecan-2-one Ketal (6). The unsaturated ketal (5) (870 mg, 0.003 M in absolute ethanol) was hydrogenated over 50 mg of palladium on charcoal to yield 832 mg of 6,12-dimethylpentadecan-2-one ketal (6); CI-MS (CH$_4$) m/z, 299 (M +1). 6,12-Dimethylpentadecan-2-one (7). A solution of 832 mg (0.003 M) of ketal (6) in acetone-10% H$_2$SO$_4$ was stirred for 3 hours. It was then extracted with hexane and the extract washed with saturated aqueous NaCl, dried over Na$_2$SO$_4$, and concentrated in vacuo to yield 695 mg (98%) of 6,12-dimethylpentadecan-2-one (7); CI-MS (CH$_4$) m/z, 255 (M +1); EI-MS (m/z), 43(100), 58(82), 59(38), 71(42), 85(24), 95(13), 97(8), 109(10), 110(15), 123(3), 137(2), 151(1), 152(0.5), 153(0.5), 165(1), 196(3), 211(2), 236(6), 254 (M +0.9); IR (CCl$_4$), 2960(s), 2930(s), 2850(s), 1735(s), 1460(m), 1375(m), 1360(m); NMR (C$_6$D$_6$), 0.875 (3H, d, J =8.1 Hz), 0.895 (3H, d, J =8.1 Hz), 0.905 (3H, t, J =6.2 Hz), 1.1–1.4 (20H, m), 1.64 (3H, s), 1.91 (2H, t, J =7.3 Hz).

The synthesized 6,12-dimethylpentadecan an-2-one (7) was purified by preparative HPLC using a 4.6-mm (ID)×25-cm stainless-steel column packed with "Adsorbosphere C18" (5 μm) by Alltech Associates, Inc., Deerfield, Ill. The methanol-water (90:10) mobile phase was pumped through the column at 1.0 ml/min, and the eluting components were detected with a Waters model R401 differential refractometer. The 6,12-dimethylpentadecan-2-one eluted from this system in 17.5 minutes. The final product purified by HPLC and GLC was >99%.

The CI and EI mass spectra and the PMR spectrum of pure synthetic racemic 6,12-dimethylpentadecan-2-one were identical with those of the isolated natural pheromone. The synthetic and natural pheromones cochromatographed, producing only one peak, on each of the two capillary GLC columns.

EXAMPLE 3

Sex Attractancy of the Natural and Synthetic Material

Field bioassays were conducted with synthesized pheromone and crude and purified natural material from the "Porapak Q" collectors. Wing traps (Pherocon 1C-type, Trece, Inc., Salinas, Calif.) were baited with various doses of these materials applied (in 200 μl of hexane) to 5.50cm filter paper circles or to methylene chloride-extracted rubber septa (A. H. Thomas, Philadelphia, Pa., No. 8753-D22).

The first test was conducted in a field of sweet potato in the vicinity of Homestead, Fla., on Nov. 6, 1985, On the morning of the test, the air temperature was about 18° C. at 9:00 AM with winds about 6-10 mph and increasing. The afternoon temperature was about 20° C. with winds 10-15 mph.

The traps were baited with filter paper formulations of 1 μg of the purified natural pheromone, a crude extract that contained 1 μg of the natural pheromone, and 1, 4, 10, 100, and 1000 μg of synthetic racemic 6,12-dimethylpentadecan-2-one and a hexane blank. Treatments were assigned randomly to traps within each replicate. Traps were placed 25 m apart in a row across the field perpendicular to the prevailing wind. Two replicates (6 traps in a row) were conducted beginning at 8:45 AM and terminating at 11:30 AM. The experiment was then moved 400 m upwind in the field and two replicates were conducted with rebaited traps in a new random order from 1:40 PM until 9:00 AM the next morning. An observer was assigned to each replicate, and the cumulative total males captured in each trap was recorded at 15-minute intervals from 8:45 to 9:30 AM (morning test), from 1:40 to 2:30 PM, at 5:00 PM, and from 8:30 to 9:00 AM the next morning. Tests were conducted during the day because preliminary trapping observations indicated that night temperatures during this period were too cool for BCB flight.

The second test was conducted in a field of mature yellow crook-neck squash in the vicinity of Gainesville, Fla., from Nov. 14 to November 20, 1985. Traps were placed 50 m apart in a row across the field and perpendicular to the prevailing wind. Treatments were 0.03, 0.1, 0.3, 1.0, 3.0, 10, and 30 mg of racemic 6,12-dimethylpentadecan-2-one, and a hexane blank formulated on rubber septa. The baits were not renewed during the test. The traps were checked daily and captured males were removed and counted, at which time the trap and bait were moved to the next trapping location in the line.

Release rates of synthetic pheromone were measured by collecting volatiles released by the septa and analyzing them by GLC. Septa were loaded with the same dose used in the field tests and aired at room temperature for 24 hours prior to release-rate measurement. Then a septum was placed in a 15-mm (ID)×20-mm-long stainless-steel tube, and compressed air, purified by passage through a charcoal filter, was passed over it at 1 liter/min for 1 hour. Volatiles entrained in the airstream were trapped on a small charcoal filter that was subsequently extracted with methylene chloride. After addition of internal standards, the extract was analyzed by capillary GLC.

Field Tests. The mean number of males captured in traps baited with filter paper formulations of natural and synthetic materials are summarized in Table 1. Since the purified natural pheromone attracted more males into traps than the crude natural material, the crude material may have included substances that either reduced the release rate or inhibited the response of the males. The captures for 1 μg natural, 4 μg synthetic, and 10 μg synthetic were not statistically different, but were different from all other means. While the number of males captured increased with increasing dose for synthetic pheromone treatments from 1 to 10 μg, linear regression analysis yielded correlation coefficient values slightly less than required for significance at the 5% level of probabilty (nontransformed data 4 =0.9945, 1 df; the coefficient did not increase with log-transformation). The responses of males to doses >10 μg was greatly reduced.

TABLE 1

MEAN CAPTURE OF MALE BCB IN TRAPS BAITED WITH NATURAL OR RACEMIC SYNTHETIC 6,12-DI-METHYLPENTADECAN-2-ONE EVAPORATED FROM FILTER PAPERS

| Amount (μg) | Treatment | Mean No. males catured per trap $X \pm SE (N = 4)^a$ |
|---|---|---|
| 0 | Hexane blank | 0.0 ± 0.0d |
| 1 | Natural crude | 32.2 ± 7.1b |
| 1 | Natural purified | 81.7 ± 20.0a |
| 1 | Synthetic | 65.5 ± 19.1b |
| 4 | Synthetic | 82.0 ± 18.6a |
| 10 | Synthetic | 104.2 ± 13.0a |
| 100 | Synthetic | 37.2 ± 12.4b |
| 1000 | Synthetic | 8.7 ± 2.9c |

$^a$Means followed by a common letter are statistically equivalent (P = 0.05, data subjected to $\sqrt{x}$ transformation) in Duncan's multiple-range test.

The observed captures for the first 2 hours of each replication of the test with filter paper formulations are shown in Table 2. The captures were not dose related for all periods and reveal a complex pattern that is probably related to nonlinear release rates from the filter papers coupled with trap interaction and the depletion of males available to react to each trap. This field was infested heavily with BCB, and reaction to the baits was nearly instantaneous. Males were seen immediately in the vicinity of the 100- and 1000-μg baited traps but did not enter these traps immediately as they did the other treatments. Again, a dose-response relationship is evident, and regression analysis yields very high correlations for the synthetic treatments 1-10 μg (r =0.983 for the total captures at 2 hours). The increase in captures at the 100 μg level, beginning 30 minutes after the taps were baited, suggests a decreasing release rate with time.

Apparently the 10 μg dose on filter paper provided a near optimum release rate of the racemic synthetic material. As can be seen from the data in Table 1, 1 μg pure natural, and 4 μg and 10 μ synthetic material showed similar responses.

The response of males to traps baited with rubber septa formulations are summarized in Table 3. Again, a relationship of increasing capture with increase dose is evident for traps baited with 30-300 μg of synthetic racemic pheromone (r=0.998 for linear regression of log dose vs. log response). Trap captures declined for treatments above 300 μg. This is the same response pattern observed with the filter paper formulations (Table 1).

The SCR was present in the test areas, and a pheromone of this species, 10-methyl-2-tridecanone, was evaporated from rubber septa baits using doses similar to those formulated in the BCB baits. Neither BCB nor SCR were captured in traps baited with the synthetic racemic pheromone of the other species.

TABLE 2

NUMBER OF MALE BCB CAPTURED PER TIME INTERVAL IN TRAPS BAITED WITH FILTER PAPER FORMULATIONS OF NATURAL OR RACEMIC SYNTHETIC 6,12-DIMETHYLPENTADECAN-2-ONE

| Treatment | | | | | | |
|---|---|---|---|---|---|---|
| Natural | | Synthetic | | | | |
| Crude (1 μg) | Pure (1 μg) | 1 μg | 4 μg | 10 μg | 100 μg | 1000 μg |
| 0–15 min after baiting | | | | | | |
| 11 | 71 | 32 | 77 | 86 | 10 | 2 |
| 15–30 min after baiting | | | | | | |
| 11 | 26 | 23 | 29 | 31 | 1 | 4 |
| 30–45 min after baiting | | | | | | |
| 4 | 24 | 18 | 15 | 23 | 39 | 6 |
| 45 min–2 hr after baiting | | | | | | |
| 37 | 145 | 83 | 76 | 138 | 42 | 7 |
| Total | | | | | | |
| 63 | 266 | 156 | 197 | 278 | 92 | 19 |

TABLE 3

MEAN NUMBER OF BCB MALES CAPTURED IN TRAPS BAITED WITH RUBBER SEPATA FORMULATIONS OF RACEMIC 6,12-DIMETHYLPENTADECAN-2-ONE

| Treatment (μg) | Mean number males captured per trap per replication (± SE) | Release rates from rubber septa (ng/hr)[a] |
|---|---|---|
| 0 | 0 | |
| 30 | 5.1 ± 0.5 | 14 |
| 100 | 13.4 ± 1.9 | 23 |
| 300 | 24.8 ± 4.3 | 39 |
| 1000 | 14.5 ± 2.1 | 124 |
| 3000 | 16.8 ± 1.9 | 476 |
| 10000 | 9.2 ± 1.1 | 1322 |
| 30000 | 5.8 ± 1.2 | 4369 |

[a] Means of two measurements; flow rate 1 liter/min, ca. 25° C.

It is understood that the foregoing detailed description is given merely by way of illustration and that modification and variation may be made therein without departing from the spirit and scope of the invention.

Having thus described the invention, we claim:

1. The substantially pure compound 6,12-dimethylpentadecan-2-one.
2. The racemic mixture of the compound of claim 1.
3. A composition which comprises the substantially pure compound 6,12-dimethylpentadecan-2-one and a carrier.
4. The composition of claim 3 in combination with an effective amount of a control agent for the banded cucumber beetle.
5. The composition of claim 4 wherein said control agent is an insecticide for the banded cucumber beetle.
6. A method of attracting adult male banded cucumber beetles, which comprises applying to the locus thereof an effective attractant amount of 6,12-dimethylpentadecan-2-one.
7. The method of claim 6 wherein 6,12-dimethylpentadecan-2-one is in combination with a suitable carrier therefore.
8. The method of claim 6 wherein 6,12-dimethylpentadecan-2-one is in combination with an effective amount of a control agent for the banded cucumber beetle.
9. A method of disruption of method of adult banded cucumber beetles, which comprises applying to the locus thereof an effective disruptant amount of 6,12-dimethylpentadecan-2-one.
10. The method of claim 9 wherein 6,12-dimethylpentadecan-2-one is in combination with a suitable carrier therefore.

* * * * *